United States Patent [19]

Stack

[11] Patent Number: 5,134,140
[45] Date of Patent: Jul. 28, 1992

[54] PSYCHOTROPIC BENZOFURAN DERIVATIVES

[75] Inventor: Gary P. Stack, Ambler, Pa.

[73] Assignee: American Home Products Corporation, New York, N.Y.

[21] Appl. No.: 719,853

[22] Filed: Jun. 21, 1991

[51] Int. Cl.$^5$ .................. C07D 405/12; A61K 31/55
[52] U.S. Cl. ............................ 514/212; 514/278; 514/414; 514/468; 548/482; 549/467; 540/524; 546/16
[58] Field of Search ............... 514/212, 278, 414, 468; 548/482; 549/467; 540/524; 546/16

[56] References Cited

U.S. PATENT DOCUMENTS

| | | | |
|---|---|---|---|
| 3,586,643 | 6/1971 | Hahn et al. | 260/2 |
| 3,915,963 | 10/1975 | Hirose et al. | 260/240 X |
| 4,873,331 | 10/1989 | Childers et al. | 544/295 |
| 4,882,432 | 11/1989 | Abou-Gharbia et al. | 544/295 |
| 4,910,302 | 3/1990 | Abou-Gharbia et al. | 540/486 |
| 4,921,958 | 5/1990 | Abou-Gharbia et al. | 544/295 |

FOREIGN PATENT DOCUMENTS

| | | | |
|---|---|---|---|
| 704705 | 4/1968 | Belgium | 544/368 |
| 837386 | 5/1968 | Belgium | 548/348 |
| 170213 | 2/1986 | European Pat. Off. | 546/16 |
| 236930 | 9/1987 | European Pat. Off. | 544/105 |
| 67/07290 | 6/1969 | South Africa | 549/467 |

OTHER PUBLICATIONS

Fozard et al., Br. J. Pharmacol 90, 273P (1987).

*Primary Examiner*—Robert T. Bond
*Attorney, Agent, or Firm*—Richard K. Jackson

[57] ABSTRACT

The antipsychotic, antidepressant, anxiolytic compounds of the formula:

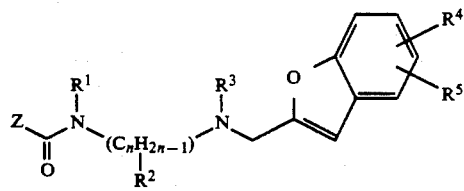

wherein Z is phenyl or phenyl substituted with alkyl, alkoxy, hydroxy, halogen or methylenedioxy or Z is one of the structures

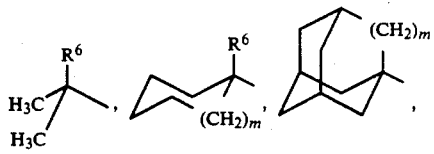

or

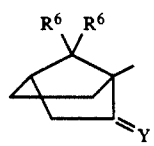

in which m is one of the integers 0, 1 or 2; $R^6$ is hydrogen or alkyl; Y is $H_2$ or O; or Z, taken with $R^1$, forms one of the structures

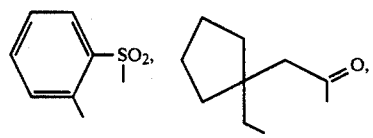

or

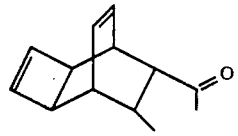

$R^1$ is hydrogen or alkyl; $R^2$ is hydrogen alkyl or phenyl; $R^3$ is hydrogen or alkyl; $R^4$ and $R^5$ are independently hydrogen, alkyl, alkoxy, aralkoxy, alkanoyloxy, hydroxy, halo, amino, mono- or dialkylamino, alkanamido of 2 to 6 carbon atoms or sulfonamido, or $R^4$ and $R^5$ together form methylenedioxy, ethylenedioxy, or propylenedioxy; n is one of the integers 2, 3 or 4; or a pharmaceutically acceptable salt thereof.

21 Claims, No Drawings

PSYCHOTROPIC BENZOFURAN DERIVATIVES

BACKGROUND OF THE INVENTION

European Patent Application EP 170,213 discloses a series of glutarimide derivatives of benzodioxan methanamine as antianxiety and antihypertensive agents. Fozard et. al. Br. J. Pharmacol. 90, 273P (1987) disclose 8-[4-(1,4-benzodioxan-2-ylmethylamino)butyl]-8-azaspiro[4.5]decane-7,9-dione (MDL 72832) as a selective and stereospecific [(−)-MDL 72832 binds 32 times as much as the dextrorotary isomer at the 5-$HT_{1A}$ receptor site] ligand for 5-$HT_{1A}$ receptors.

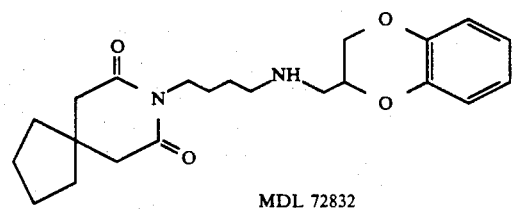

MDL 72832

European Patent EP 236,930 discloses a series of 2-substituted-alkyl-1,2-benzisothiazole-3-one 1,1-dioxide derivatives useful as anxiolytic and antihypertensive agents. Specifically claimed is 2-(4-(2,3-dihydro-1,4-benzodiox-2-yl)methylamino)butyl)-1,2-benzisothiazol-3(2H)-one 1,1-dioxide.

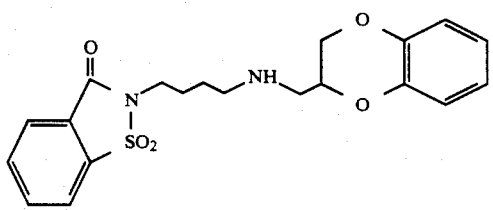

U.S. Pat. No. 4,910,302 discloses a series of psychotropic polycyclic imides such as

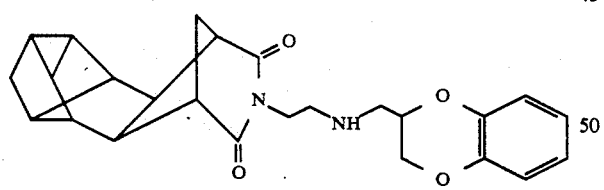

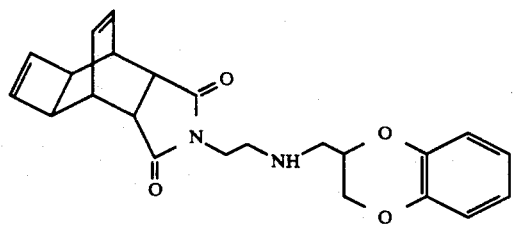

as antianxiety and antipsychotic agents.

U.S. Pat. No. 4,921,958; 4,873,331, and 4,882,432 describe adamantyl esters, carbonates, ureas, urethans, and reverse amides as anxiolytic antidepressant and antihypertensive agents.

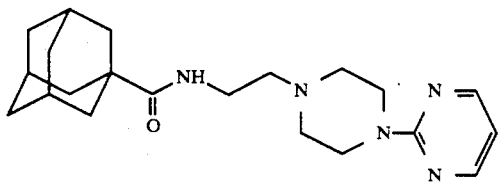

British Patent Application GB 75-1934 (corresponding to Belg. 837,386) discloses a series of 1,4-benzodioxyanyl and benzofuranyl methylamines (defined as indicated below) as hypotensives, vasodilators and for treating cardiovascular disorders. The compound of structure II in which R=$CH_2C(:NH)NHOH$ is claimed to be an antidepressant. S. African 67 07,290 similarly discloses a series of 2-(phenoxyalkylaminomethyl)-2,3-dihydrobenzofurans as blood pressure lowering, and adrenolytic and adrenergic blocking agents.

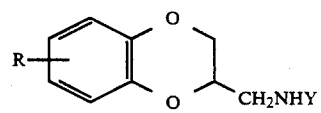

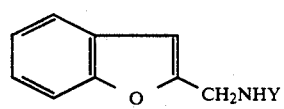

in which

R is H or 1–5 C alkyl;
Y is 2–5 alkenyl, —$CH_2CN$, —$CH_2C(:NH)NH_2$, —$CH_2C(:NH)NHOH$,

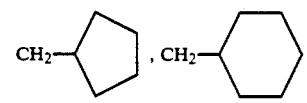

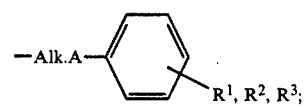

in which
Alk is 1–2 C alkylene;
A is O or CO;
$R^1$, $R^2$, $R^3$ are H, OH, 1–5 C alkyl, 1–5 C alkoxy or halogen; or
$R^1$ and $R^2$ are methylenedioxy.

Belgian Patent Application Belg. 704,705 discloses a series of 2-aminomethylbenzofurans of formula III wherein $R^1$ is 2, 3 or 4-pyridyl, 3 or 4-methoxyphenyl, 3 or 4-chlorophenyl, or 3 or 4-methylphenyl, $R^2$ is ethyl, n-propyl, or isopropyl, substituted by dimethylamino, diethylamino, piperidinyl, N-methylpiperazinyl, 4-(2-dimethylaminoethyl)piperazinyl, or 4-(3-dimethylaminopropyl)piperazinyl, as antitussives and antihistamines.

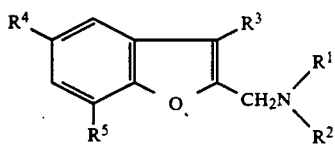

U.S. Pat. No. 3,915,963 discloses a series of 7-methoxy-2,3-dihydrobenzofuran derivatives of structure IV, in which R is cinnamyl, PhCHMe, Ph(CH2)$_n$ (n=1-3), as analgesics. Japan Kokai 73 13,360 discloses similar compounds, in which R is β-methoxy propyl, β-hydroxypropyl, cyclopentylcarbonyl, γ-phenylpropargyl and β-phenethyl, as analgesics.

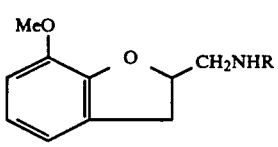

DESCRIPTION OF THE INVENTION

In accordance with this invention, there is provided a group of novel antidepressant/anxiolytic agents of the formula:

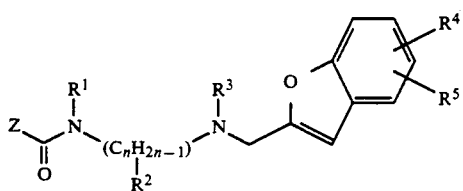

wherein

Z is phenyl or phenyl substituted with alkyl of 1 to 4 carbon atoms, alkoxy of 1 to 4 carbon atoms, hydroxy, halogen or methylenedioxy or Z is one of the structures

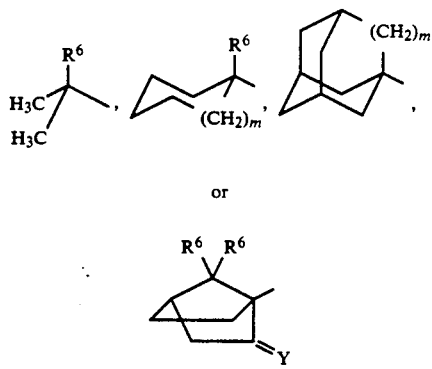

in which
m is one of the integers 0, 1 or 2;
$R^6$ is hydrogen or alkyl of 1 to 4 carbon atoms;
Y is H$_2$ or O; or
Z, taken with $R^1$, forms one of the structures

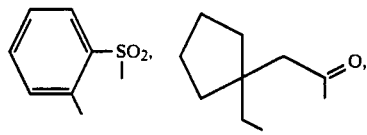

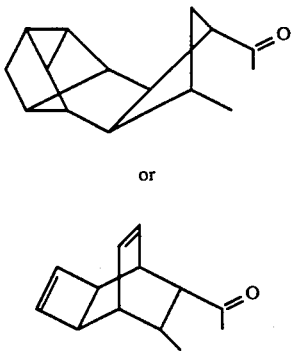

$R^1$ is hydrogen or alkyl of 1 to 4 carbon atoms;
$R^2$ is hydrogen, alkyl of 1 to 4 carbon atoms or phenyl;
$R^3$ is hydrogen or alkyl of 1 to 4 carbon atoms;
$R^4$ and $R^5$ are independently hydrogen, alkyl of 1 to 4 carbon atoms, alkoxy of 1 to 4 carbon atoms, aralkoxy or 7 to 12 carbon atoms, alkanoyloxy of 2 to 4 carbon atoms, hydroxy, halo, amino, mono- or dialkylamino in which each alkyl group has 1 to 4 carbon atoms, alkanamido of 2 to 6 carbon atoms or sulfonamido, or $R^4$ and $R^5$ together form methylenedioxy, ethylenedioxy, or propylenedioxy;
n is one of the integers 2, 3 or 4;
or a pharmaceutically acceptable salt thereof.

Of these compounds, the preferred members are those in which Z is defined above, $R^1$ is hydrogen or combines with Z as described above, $R^2$ is hydrogen, $R^3$, $R^4$ and $R^5$ are defined as above and n is the integer 2. Most preferred are those members in which Z is adamantyl or noradamantyl, $R^1$, $R^2$, $R^3$ and $R^4$ are hydrogen, $R^5$ is 7-methoxy or hydroxy and n is 2.

The pharmaceutically acceptable salts are those derived from such organic and inorganic acids as: acetic, lactic, citric, tartaric, succinic, maleic, malonic, hydrochloric, hydrobromic, phosphoric, nitric, sulfuric, methanesulfonic, and similarly known acceptable acids.

The compounds of this invention are prepared by conventional methods. For example, the appropriately substituted benzofuran methanamine is combined with a suitable acid halide in the presence of an acid scavenger such as diisopropylethylamine in a solvent such as dichloromethane (1), or with a suitable anhydride, followed by a period of reflux in a high boiling solvent such as xylene, with water removal by means of a Dean-Stark trap (2). The 1,2-benziothiazol-3(2H)-one 1,1-dioxide derivatives may be prepared by reaction of the appropriately substituted benzofuran methanamine with methyl 2-(chlorosulfonyl)-benzoate in the presence of a tertiary amine such as diisopropylethylamine, followed by treatment of the resulting amide with a base such as dimethylaminopyridine (DMAP) in refluxing xylene (3).

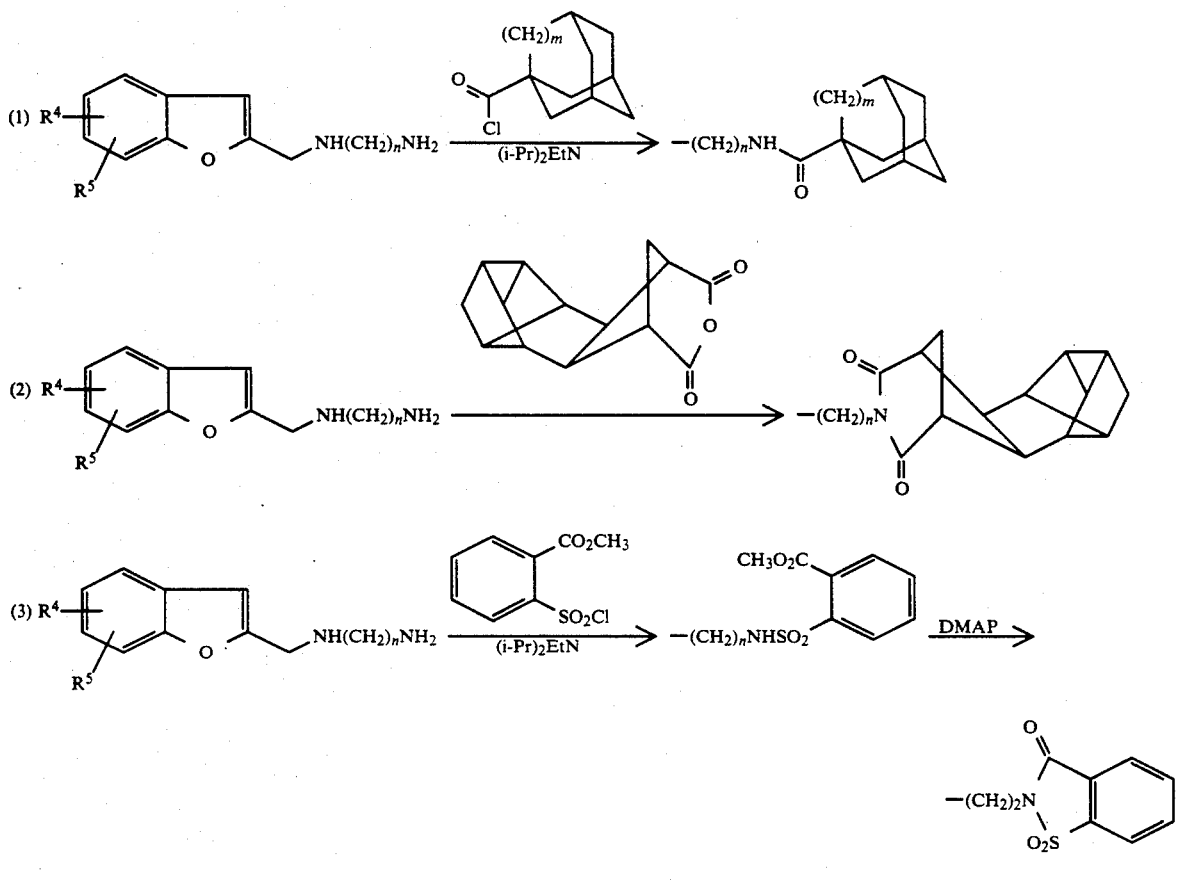

The bicyclic carboxylic acids described by Z are known compounds or they can be readily synthesized by one schooled in the art. Adamantane and noradamantane-1-carboxylic acids are commercially available; ketopinic acid can be prepared from camphorsulfonyl chloride by the method of Bartlett and Knox (Organic Synthesis, Vol. 45, p. 55) and can be converted to apocamphane-1-carboxylic acid by the method described in J. Am. Chem. Soc., 61, 3184 (1939). The benzofuran methanamines themselves are known compounds, or they can readily be derived from the appropriate salicylaldehyde by the procedure illustrated below:

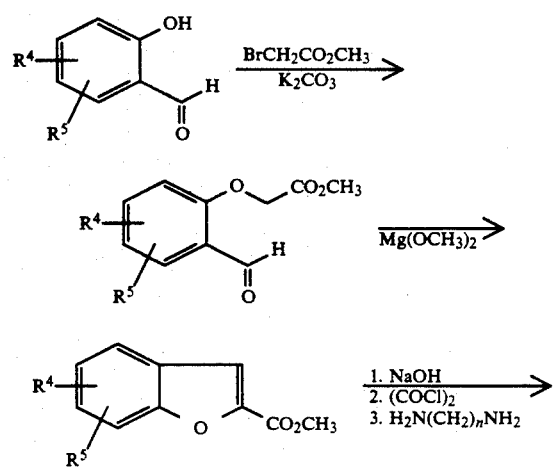

-continued

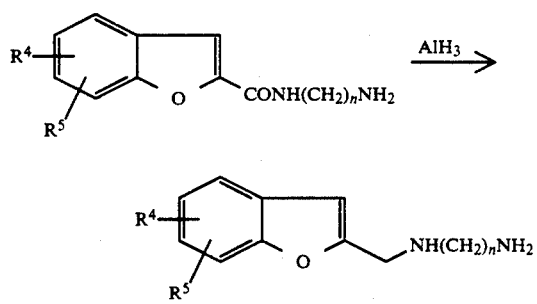

Like the standard anxiolytic agent buspirone, the compounds of this invention possess high affinity for the serotonin $5-HT_{1A}$ receptor, and consequently, they are useful for treatment of diseases of the central serotoninergic system, such as anxiety, depression, schizophrenia, sexual dysfunction, eating disorders, obsessive-compulsive disorder, addiction and related problems. Unlike buspirone, the compounds of this invention possess only modest affinity for dopamine $D_2$ receptors, and are therefore unlikely to cause the movement disorders and dyskinesias characteristic of classical antipsychotic agents such as haloperidol.

Modest affinity for the dopamine $D_2$ receptor was established by the standard experimental test procedure of Fields, et al., Brain Res., 136, 578 (1977) and Yamamura et al., eds., Neurotransmitter Receptor Binding, Raven Press, N.Y. (1978) wherein homogenized limbic brain tissue is incubated with $^3H$-spiroperidol and various concentrations of test compound, filtered and washed and shaken with Hydrofluor scintillation cocktail (National Diagnostics) and counted in a Packard 460 CD scintillation counter. The results of this testing with compounds of this invention are given below.

High affinity for the serotonin $5\text{-HT}_{1A}$ receptor was established by testing the claimed compound's ability to displace [$^3$H] 8-OHDPAT (dipropylaminotetralin) from the $5\text{-HT}_{1A}$ serotonin receptor following the procedure of Hall et al., J. Neurochem. 44, 1685 (1985). This procedure is employed to analogize this property of the claimed compounds with that of buspirone, which is a standard for anxiolytic activity, and, like the compounds of this invention, displays potent affinity for the $5\text{-HT}_{1A}$ serotonin receptor subtype. The anxiolytic activity of buspirone is believed to be, at least partially, due to its $5\text{-HT}_{1A}$ receptor affinity (Vander Maclen et al., Eur. J. Pharmacol. 1986, 129 (1–2) 133–130).

The results of the two standard experimental test procedures described in the preceding two paragraphs were as follows:

| Compound | D-2 Binding (% Inhibition at 1 μM) | $5\text{-HT}_{1A}$ Binding (% Inhibition at 0.1 μM) |
|---|---|---|
| Example 1 | | 31% |
| Example 2 | 29% | 100% (IC$_{50}$ = 0.5 nM) |
| Example 3 | 72% | 61% |
| Example 4 | 49% | 59% |
| Example 5 | 4% | 87% |
| Example 6 | 70% | 87% |
| Example 7 | | 99% |
| Example 8 | | 92% |
| Example 9 | | 63% |
| Example 10 | | 90% (IC$_{50}$ = 9 nM) |
| Example 11 | | 38% |
| Example 12 | | 20% |
| Example 13 | | 95% |
| Example 15 | | 64% |
| Example 16 | | 97% |
| Example 17 | | 88% |

Certain of the compounds of this invention were also compared to buspirone in their ability to either produce or antagonize the serotonin syndrome according to the procedure of Smith and Peroutka, Pharmacol. Biochem. Behav. 24:1513–1519, 1986, in which 250–350 g male Sprague-Dawley CD rats (Charles River) are given either test compound or vehicle and placed individually into plexiglass observation cages. Agonist activity of the compound is determined by scoring for the presence of the serotonin syndrome (forepaw treading, head weaving, tremor, hindlimb abduction, flattened body posture, and Straub tail) during the first 15 minutes after compound administration. Antagonist activity is then determined by a challenge with either of the $5\text{-HT}_{1A}$ agonists 5-methoxy-N,N-dimethyltryptamine (5-MeODMT) or 8-hydroxydipropylaminotetralin. Buspirone produced the syndrome with an ED$_{50}$ of 7.3 mg/kg and antagonized 5-MeODMT-induced syndrome with an ED$_{50}$ of 4.6 mg/kg, and thus was characterized as a partial agonist. The compound of Example 2 and the compound of Example 7 were found to mimic the ability of buspirone to antagonize the serotonin syndrome with ED$_{50}$'s of 11.7 and 15.4 mg/kg, respectively.

Hence, the compounds of this invention demonstrated potent and selective affinity for the serotonin $5\text{-HT}_{1A}$ receptor subtype, and are therefore useful in the treatment of multi-CNS disorders amenable to treatment with anxiolytic, antidepressant and antipsychotic agents with little possibility for the production of extrapyramidal side effects. As such, the compounds of this invention are useful in the treatment of patients suffering from psychoses, depression or anxiety, by oral or parenteral administration at a subjective dose level sufficient to relieve the symptoms of the CNS disorder.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweetners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis or state of anxiety and the size, age and response pattern of the patient.

The following examples illustrate the production of representative compounds of this invention.

EXAMPLE 1

3a, 4, 4a, 6a, 7, 7a-Hexahydro-2-[2-[[(7-methoxy-2-benzofuranyl)methyl]amino]ethyl]-4,7-etheno-1H-cyclobut[f]isoindole-1,3(2H)-dione 2-[(7-Methoxy-2-benzofuranyl)methyl]amino]ethylamine (0.80 g, 3.6 mmole) and hexahydro-4,7-etheno-1H-cyclobut[f]isobenzofuran-1,3-(2H)-dione (735 mg, 3.6 mmole) were combined in 100 ml of xylene and the mixture was refluxed for 48 hours under nitrogen, with water removal being accomplished by means of a Dean-Stark trap. Upon cooling, the mixture was column chromatographed on 100 g of silica gel with toluene, then chloroform, and finally 2% methanol/chloroform as eluant. The product-containing fractions were combined and concentrated in vacuum, and the residue crystallized from 50 ml of isopropanol with the addition of 2 ml of 4N isopropanolic HCl. The product thus obtained was recrystallized from isopropanol to give 630 mg of the title compound as a white solid, monohydrochloride, m.p. 236°–239° C.

Elemental Analysis for: $C_{24}H_{24}N_2O_4 \cdot HCl$: Calcd: C, 65.38; H, 5.71; N, 6.35. Found: C, 65.54; H, 5.60; N, 6.11.

EXAMPLE 2

N-[2-[[(7-Methoxy-2-benzofuranyl)methyl]amino]ethyl]tricyclo[3.3.1.1$^{3,7}$]decane-1-carboxamide To a solution of 2-[(7-methoxy-2-benzofuranyl)methyl]amino]ethylamine (1.10 g, 5.0 mmole) and diisopropylethylamine (1.3 g, 10 mmole) in 100 ml of dichloromethane cooled in an ice-water bath was added adamantane-1-carbonyl chloride (0.93 g, 5.0 mmole). The mixture was allowed to come to room temperature and stir overnight under nitrogen. It was then washed with saturated aqueous sodium bicarbonate and saturated aqueous sodium chloride, dried over sodium sulfate, filtered and evaporated in vacuum. The residue was column chromatographed on 50 g of silica gel using chloroform as eluant and the product thus obtained was crystallized from isopropanol with the addition of 4N HCl/isopropanol and 4 volumes of diethyl ether to give 750 mg of the title compound as a white solid, monohydrochloride, quarter hydrate, m.p. 105°–110° C.

Elemental Analysis for: $C_{23}H_{30}N_2O_3 \cdot HCl \cdot \frac{1}{4}H_2O$: Calcd: C, 65.23; H, 7.50; N, 6.62. Found: C, 65.42; H, 7.34; N, 6.52.

EXAMPLE 3

8-[2-[[(7-Methoxy-2-benzofuranyl)methyl]amino]ethyl]-8-azaspiro[4.5]decane-7,9-dione 2-[(7-Methoxy-2-benzofuranyl)methyl]amino]ethylamine (1.1 g, 5.0 mmole) and 3,3-tetramethylene glutaric anhydride (0.84 g, 5.0 mmole) were combined in 100 ml of xylene and the mixture was refluxed for 48 hours under nitrogen, with water removal being accomplished by means of a Dean-Stark trap. Upon cooling, the mixture was column chromatographed on 100 g of silica gel with first toluene, then chloroform as eluant. The product-containing fractions were combined and concentrated in vacuum, and the residue crystallized from 50 ml of isopropanol with the addition of 4N isopropanolic HCl and 4 volumes of diethyl ether to give 165 mg of the title compound as a white solid, monohydrochloride, m.p. 156°–158° C.

Elemental Analysis for: $C_{22}H_{26}N_2O_4 \cdot HCl$: Calcd: C, 61.99; H, 6.69; N, 6.89. Found: C, 61.77; H, 6.55; N, 6.92.

EXAMPLE 4

Decahydro-3-[2-[[(7-methoxy-2-benzofuranyl)methyl]amino]ethyl]-1,5-methano-6,7,9-metheno-2H-pentaleno[1,2-d]azepine-2,4(3H)-dione 2-[(7-Methoxy-2-benzofuranyl)methyl]amino]ethylamine (1.1 g, 5.0 mmole) and decahydro-1,5-methano-6,7,9-methenopentaleno[1,2-d]oxepine-2,4(1H,5H)dione (1.15 g, 5.0 mmole) were combined in 100 ml of xylene and the mixture was refluxed for 48 hours under nitrogen, with water removal being accomplished by means of a Dean-Stark trap. Upon cooling, the mixture was column chromatographed on 50 g of silica gel with first toluene and then chloroform as eluant. The product-containing fractions were combined and concentrated in vacuum, and the residue crystallized from isopropanol with the addition of 4N isopropanolic HCl and 4 volumes of diethyl ether to give 250 mg of the title compound as a tan solid, monohydrochloride, m.p. 199°–200° C.

Elemental Analysis for: $C_{26}H_{28}N_2O_4 \cdot HCl$: Calcd: C, 66.59; H, 6.23; N, 5.97. Found: C, 66.51; H, 6.48; N, 5.66.

EXAMPLE 5

N-[2-[[(7-Methoxy-2-benzofuranyl)methyl]amino]ethyl]-7,7-dimethyl-2-oxobicyclo[2.2.1]heptane-1-carboxamide (+)-Ketopinic acid (1.5 g, 8.0 mmole), prepared from (+)-10-camphorsulfonyl chloride by the procedure of Bartlett and Knox, Org. Syn., 45, p. 55, was converted to the acid chloride by treatment of a solution of the compound in 50 ml of methylene chloride with 2.0 ml (23 mmole) of oxalyl chloride. After stirring for 2 hours at room temperature, the mixture was concentrated in vacuum. It was then redissolved in 50 ml of methylenechloride and added dropwise to a solution of 1.8 g (8.0 mmole) of 2-[(7-methoxy-2-benzofuranyl)methyl]amino]ethylamine and 1.3 g (10 mmole) of diisopropylethylamine in 100 ml of dichloromethane in an ice-water bath. After stirring overnight at room temperature, the mixture was washed with saturated sodium bicarbonate solution, with saturated sodium chloride, dried over sodium sulfate, filtered and concentrated in vacuum. The residue was column chromatographed on 100 g of silica gel with chloroform as eluant and the title compound thus obtained was crystallized from 75 ml of isopropanol with the addition of 4 ml of 4N HCl/isopropanol and 225 ml of diethyl ether. This procedure gave 1.1 g of title compound as a white solid, monohydrochloride, m.p. 177°–178° C.

Elemental Analysis for: $C_{22}H_{28}N_2O_4 \cdot HCl$: Calcd: C, 62.77; H, 6.94; N, 6.66. Found: C, 62.63; H, 6.51; N, 6.68.

EXAMPLE 6

N-[2-[[(7-Methoxy-2-benzofuranyl)methyl[amino]ethyl]-4-fluorobenzamide

To a solution of 2-[(7-methoxy-2-benzofuranyl)methyl]amino]ethylamine (2.2 g, 10 mmole) and diisopropylethylamine (1.3 g, 10 mmole) in 100 ml of dichloromethane cooled in an ice-water bath was added dropwise a solution of p-fluorobenzoyl chloride (1.6 g, 10 mmole) in 50 ml of dichloromethane. The mixture was allowed to come to room temperature and stir overnight under nitrogen. It was then washed with 100 ml portions of saturated aqueous sodium bicarbonate and saturated aqueous sodium chloride, dried over sodium sulfate, filtered and evaporated in vacuum. The residue was column chromatographed on 100 g of silica gel using chloroform as eluant and the product thus obtained was crystallized from isopropanol with the addition of 3 ml of 4N HCl/isopropanol to give 1.0 g of the title compound as a white solid, monohydrochloride, m.p. 207°–208° C.

Elemental Analysis for: $C_{19}H_{19}N_2O_3F \cdot HCl$: Calcd: C, 60.24; H, 5.32; N, 7.39. Found: C, 60.14; H, 5.40; N, 7.02.

EXAMPLE 7

N-[2-[[(7-Methoxy-2-benzofuranyl)methyl]amino]ethyl]hexahydro-2,5-methanopentalene-3a(1H)-carboxamide To 1.7 g (10 mmole) of noradamantane carboxylic acid in 100 ml of dichloromethane was added 3.0 ml (35 mmole) of oxalyl chloride and two drops of DMF. The mixture was stirred at room temperature for two hours and then concentrated in vacuum. It was redissolved in 25 ml of dichloromethane and added to an ice cold solution of 2.2 g (10 mmole) 2-[(7-methoxy-2-benzofuranyl)methyl]amino]ethylamine and 1.3 g (10 mmole) diisopropylethylamine in 100 ml of dichloromethane. The mixture was allowed to stir overnight at room temperature. It was then washed with 100 ml portions of saturated sodium bicarbonate solution and saturated brine, dried over sodium sulfate, filtered and concentrated in vacuum. The residue was column chromatographed on 100 g of silica gel with chloroform as eluant, and the product crystallized from 50 ml of isopropanol with the addition of 4 ml of 4N HCl/isopropanol and 250 ml of diethyl ether. This yielded 2.2 g of title compound as the monohydrochloride, m.p. 103°–107° C.

Elemental Analysis for: $C_{22}H_{28}N_2O_3 \cdot HCl$: Calcd: C, 65.26; H, 7.22; N, 6.92. Found: C, 64.90; H, 7.56; N, 7.00.

EXAMPLE 8

N-[2-[[(7-Methoxy-2-benzofuranyl)methyl]amino]ethyl]-1-methyl-1-cyclohexane carboxamide To 0.9 g (6.0 mmole) of α-methylcyclohexane carboxylic acid in 100 ml of dichloromethane was added 1.0 ml (11.5 mmole) of oxalyl chloride and two drops of DMF. The mixture was stirred at room temperature for two hours and then concentrated in vacuum. It was redissolved in 50 ml of dichloromethane and added to an ice cold solution of 1.32 g (6.0 mmole) 2-[(7-methoxy-2-benzofuranyl)methyl]amino]ethylamine and 0.80 g (6.0 mmole) diisopropylethylamine in 100 ml of dichloroemthane. The mixture was allowed to stir overnight at room temperature. It was then washed with 50 ml portions of saturated sodium bicarbonate solution and saturated brine, dried over sodium sulfate, filtered and concentrated in vacuum. The residue was column chromatographed on 100 g of silica gel with chloroform as eluant, and an attempt was made to crystallize the product from 50 ml of isopropanol with the addition of 4 ml of 4N HCl/isopropanol and 250 ml of diethyl ether. When this procedure failed to produce crystals, the mixture was concentrated in vacuum and 50 ml of acetone and 50 ml of diethyl ether added. This yielded 0.60 g of title compound as a monohydrochloride, quarter hydrate, amorphous, white solid with no true melting point.

Elemental Analysis for: $C_{20}H_{28}N_2O_3 \cdot HCl \cdot \frac{1}{4}H_2O$: Calcd: C, 62.32; H, 7.71; N, 7.27. Found: C, 62,27; H, 7.56; N, 7.14.

EXAMPLE 9

N-[2-[[(6,7-Dimethoxy-2-benzofuranyl)methyl]amino]ethyl]tricyclo[3.3.1.1$^{3,7}$]decane-1-carboxamide To a solution of 2-[(6,7-dimethoxy-2-benzofuranyl)methyl]amino]ethylamine (2.1 g, 8.4 mmole) and diisopropylethylamine (1.3 g, 10 mmole) in 100 ml of dichloromethane cooled in an ice-water bath was added adamantane-1-carbonyl chloride (1.6 g, 8.4 mmole) in 50 ml of dichloromethane. The mixture was allowed to come to room temperature and stir overnight under nitrogen. It was then washed with 100 ml portions of saturated aqueous sodium bicarbonate and saturated aqueous sodium chloride, dried over sodium sulfate, filtered and evaporated in vacuum. The residue was column chromatographed on 100 g of silica gel using chloroform as eluant and the product thus obtained was crystallized from 75 ml of isopropanol with the addition of 4 ml of 4N HCl/isopropanol and 225 ml of diethyl ether to give 1.6 g of the title compound as a white solid, monohydrochloride, m.p. 206°–207° C.

Elemental Analysis for: $C_{24}H_{32}N_2O_4 \cdot HCl$: Calcd: C, 64.20; H, 7.41; N, 6.24. Found: C, 64.16; H, 7.47; N, 5.99.

EXAMPLE 10

N-[2-[[(7-Methoxy-2-benzofuranyl)methyl]methylamino]ethyl]tricyclo[3.3.1.1$^{3,7}$]decane-1-carboxamide N-[2-[[(7-Methoxy-2-benzofuranyl)methyl]amino]ethyl]tricyclo[3.3.1.1$^{3,7}$]decane-1-carboxamide hydrochloride hemihydrate (1.0 g, 2.4 mmole), prepared as in Example 2, was dissolved in 100 ml of ethanol and 5 ml of 38% aqueous formaldehyde and 500 mg of 10% palladium on carbon were added. The mixture was hydrogenated at 50 psi on a Parr apparatus for 24 hours. The mixture was then filtered through celite and 300 ml of ether added. It was washed with 100 ml portions of saturated aqueous sodium bicarbonate and saturated aqueous sodium chloride, dried over sodium sulfate, filtered and evaporated in vacuum. The residue was purified by column chromatography on 100 g of silica gel with chloroform as eluant and recrystallized from acetone/diethyl ether with the addition of 3 ml of 4N HCl/isopropanol to give 560 mg of the title compound as a white solid, monohydrochloride, quarter hydrate, m.p. 156°–158° C.

Elemental Analysis for: $C_{24}H_{32}N_2O_3 \cdot HCl \cdot \frac{1}{4}H_2O$: Calcd: C, 65.89; H, 7.72; N, 6.40. Found: C, 66.08; H, 7.76; N, 6.33.

EXAMPLE 11

N-[2-[[(7-Methoxy-2-benzofuranyl)methyl]amino]ethyl]-2,2-dimethylpropanamide

To a solution of 2-[(7-methoxy-2-benzofuranyl)methyl]amino]ethylamine (2.2 g, 10 mmole) and diisopropylethylamine (1.3 g, 10 mmole) in 100 ml of dichloromethane cooled in an ice-water bath was added dropwise a solution of pivaloyl chloride (1.2 g, 10 mmole) in 50 ml of dichloromethane. The mixture was allowed to come to room temperature and stir overnight under nitrogen. It was then washed with 100 ml portions of saturated aqueous sodium bicarbonate and saturated aqueous sodium chloride, dried over sodium sulfate, filtered and evaporated in vacuum. The residue was column chromatographed on 50 g of silica gel using chloroform as eluant and the product thus obtained was crystallized from a mixture of 100 ml each of acetone and diethyl ether with the addition of 5 ml of 4N HCl/isopropanol to give 1.2 g of the title compound as a white solid, monohydrochloride, quarter hydrate, m.p. 81°–82° C.

Elemental Analysis for: $C_{17}H_{24}N_2O_3 \cdot HCl \cdot \frac{1}{4}H_2O$: Calcd: C, 59.12; H, 7.35; N, 8.11. Found: C, 58.85; H, 7.58; N, 7.90.

EXAMPLE 12

N-[2-[[(6-Phenylmethoxy-2-benzofuranyl)methyl]amino]ethyl]tricyclo[3.3.1.1$^{3,7}$]decane-1-carboxamide To 0.81 g (4.5 mmole) of 1-adamantane carboxylic acid in 50 ml of dichloromethane was added 1.0 ml (11.5 mmole) of oxalyl chloride and two drops of DMF. The mixture was stirred at room temperature overnight and then concentrated in vacuum. It was redissolved in 25 ml of dichloromethane and added to an ice cold solution of 1.32 g (4.5 mmole) 2-[(6-benzyloxy-2-benzofuranyl)methyl]amino]ethylamine and 0.65 g (5.0 mmole) diisopropylethylamine in 50 ml of dichloromethane. The mixture was allowed to stir overnight at room temperature. It was then washed with 50 ml portions of saturated sodium bicarbonate solution and saturated brine, dried over sodium sulfate, filtered and concentrated in vacuum. The residue was column chromatographed on 100 g of silica gel with chloroform as eluant, and the product crystallized from 25 ml of isopropanol with the addition of 4 ml of 4N HCl/isopropanol and 75 ml of diethyl ether. This yielded 0.34 g of title compound, m.p. 206°–206.5° C.

Elemental Analysis for: $C_{29}H_{34}N_2O_3 \cdot HCl$: Calcd: C, 70.36; H, 7.13; N, 5.66. Found: C, 70.47; H, 7.07; N, 5.63.

EXAMPLE 13

N-[2-[[(7-Fluoro-2-benzofuranyl)methyl]amino]ethyl]tricyclo[3.3.1.1$^{3,7}$]decane-1-carboxamide To 0.63 g (3.5 mmole) of 1-adamantane carboxylic acid in 50 ml of dichloromethane was added 0.8 ml (9.2 mmole) of oxalyl chloride and two drops of DMF. The mixture was stirred at room temperature overnight and then concentrated in vacuum. It was redissolved in 25 ml of dichloromethane and added to an ice cold solution of 0.73 g (3.5 mmole) 2-[(7-fluoro-2-benzofuranyl)methyl]amino]ethylamine and 0.70 ml (4.0 mmole) diisopropylethylamine in 50 ml of dichloromethane. The mixture was allowed to stir overnight at room temperature. It was then washed with 50 ml portions of saturated sodium bicarbonate solution and saturated brine, dried over sodium sulfate, filtered and concentrated in vacuum. The residue was column chromatographed on 100 g of silica gel with chloroform as eluant, and the product crystallized from 25 ml of isopropanol with the addition of 4 ml of 4N HCl/isopropanol and 75 ml of diethyl ether. This yielded 0.60 g of title compound, m.p. 205°–205.5° C.

Elemental Analysis for: $C_{22}H_{27}N_2O_2F \cdot HCl$: Calcd: C, 64.94; H, 6.94; N, 6.88. Found: C, 64.75; H, 7.03; N, 6.75.

EXAMPLE 14

N-[2-[[(5-Phenylmethoxy-2-benzofuranyl)methyl]amino]ethyl]tricyclo[3.3.1.1$^{3,7}$]decane-1-carboxamide To 1.1 g (6.1 mmole) of 1-adamantane carboxylic acid in 50 ml of dichloromethane was added 1.36 ml (15.6 mmole) of oxalyl chloride and two drops of DMF. The mixture was stirred at room temperature overnight and then concentrated in vacuum. It was redissolved in 25 ml of dichloromethane and added to an ice cold solution of 1.8 g (6.1 mmole) 2-[(5-benzyloxy-2-benzofuranyl)methyl]amino]ethylamine and 1.22 g (7.6 mmole) diisopropylethylamine in 50 ml of dichloromethane. The mixture was allowed to stir overnight at room temperature. It was then washed with 50 ml portions of saturated sodium bicarbonate solution and saturated brine, dried over sodium sulfate, filtered and concentrated in vacuum. The residue was column chromatographed on 100 g of silica gel with chloroform as eluant, and the product crystallized from 30 ml of isopropanol with the addition of 6 ml of 4N HCl/isopropanol and 100 ml of diethyl ether. This yielded 0.41 g of title compound as a monohydrochloride, m.p. 169°–170° C.

Elemental Analysis for: $C_{29}H_{34}N_2O_3 \cdot HCl$: Calcd: C, 70.36; H, 7.13; N, 5.66. Found: C, 70.10; H, 7.38; N, 5.53.

EXAMPLE 15

N-[2-[[(5-Hydroxy-2-benzofuranyl)methyl]amino]ethyl]tricyclo[3.3.1.1$^{3,7}$]decane-1-carboxamide N-[2-[[(5-Phenylmethoxy-2-benzofuranyl)methyl]amino]ethyl]tricyclo[3.3.1.1$^{3,7}$]decane-1-carboxamide (0.70 g, 1.5 mmole) was dissolved in 100 ml of ethanol and 160 mg of 10% palladium on carbon was added. The mixture was hydrogenated at 50 psi on a Parr apparatus overnight. The mixture was then filtered through celite and concentrated in vacuum. The residue was crystallized from 25 ml of isopropanol with the addition of 7 ml of 4N HCl/isopropanol and 100 ml of diethyl ether to give 320 mg of the title compound as a white solid, monohydrochloride, hydrate, m.p. 140°–143° C.

Elemental Analysis for: $C_{22}H_{28}N_2O_3 \cdot HCl \cdot H_2O$: Calcd: C, 62.47; H, 7.39; N, 6.62. Found: C, 62.44; H, 7.41; N, 6.52.

EXAMPLE 16

N-[2-[[(7-Chloro-2-benzofuranyl)methyl]amino]ethyl]tricyclo[3.3.1.1$^{3,7}$]decane-1-carboxamide To 1.8 g (10 mmole) of 1-adamantane carboxylic acid in 100 ml of dichloromethane was added 2.0 ml (23 mmole) of oxalyl chloride and two drops of DMF. The mixture was stirred at room temperature for one hour and then concentrated in vacuum. It was redissolved in 25 ml of dichloromethane and added to an ice cold solution of 2.3 g (10 mmole) 2-[(7-chloro-2-benzofuranyl)methyl]amino]ethylamine and 1.3 g (10 mmole) diisopropylethylamine in 100 ml of dichloromethane. The mixture was allowed to stir overnight at room temperature. It was then washed with 100 ml portions of saturated sodium bicarbonate solution and saturated brine, dried over sodium sulfate, filtered and concentrated in vacuum. The residue was column chromatographed on 100 g of silica gel with chloroform as eluant, and the product crystallized from 75 ml of isopropanol with the addition of 5 ml of 4N HCl/isopropanol and 200 ml of diethyl ether. This yielded 0.58 g of the title compound as the monohydrochloride, m.p. 215°-216° C.

Elemental Analysis for: $C_{22}H_{27}N_2O_2Cl \cdot HCl$: Calcd: C, 62.41; H, 6.67; N, 6.62. Found: C, 62.25; H, 6.68; N, 6.56.

EXAMPLE 17

N-[2-[[(6-Hydroxy-2-benzofuranyl)methyl]amino]ethyl]tricyclo[3.3.1.1^{3,7}]decane-1-carboxamide N-[2-[[(6-Phenylmethoxy-2-benzofuranyl)methyl]amino]ethyl]tricyclo[3.3.1.1^{3,7}]decane-1-carboxamide (4.74 g, 10 mmole) was dissolved in 100 ml of ethanol and 1.0 g of 10% palladium on carbon was added. The mixture was hydrogenated at 50 psi on a Parr apparatus overnight. The mixture was then filtered through celite and concentrated in vacuum. The residue was column chromatographed on 100 g of silica gel using 5% methanol/chloroform as eluant and the crude product thus obtained was crystallized from 15 ml of ethanol with the addition of 8 ml of 4N HCl/isopropanol and 100 ml of diethyl ether to give 1.6 g of the title compound as a white solid, monohydrochloride, quarter hydrate, m.p. 136°-139° C.

Elemental Analysis for: $C_{22}H_{28}N_2O_3 \cdot HCl \cdot \frac{1}{4}H_2O$: Calcd: C, 64.53; H, 7.26; N, 6.84. Found: C, 64.77; H, 7.25; N, 6.68.

What is claimed is:
1. A compound of the formula:

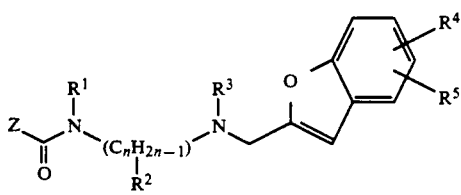

wherein

Z is phenyl or phenyl substituted with alkyl of 1 to 4 carbon atoms, alkoxy of 1 to 4 carbon atoms, hydroxy, halogen or methylenedioxy or Z is one of the structures

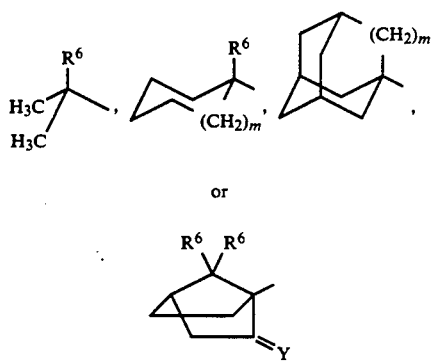

in which m is one of the integers 0, 1 or 2;

$R^6$ is hydrogen or alkyl of 1 to 4 carbon atoms;

Y is $H_2$ or O; or

Z, taken with $R^1$, forms one the structures

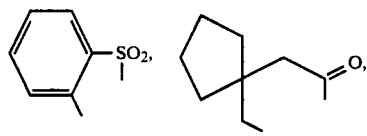

or

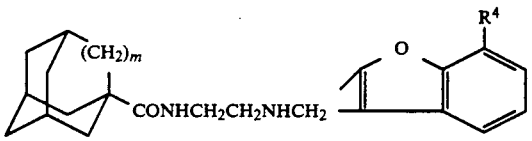

$R^1$ is hydrogen or alkyl of 1 to 4 carbon atoms;

$R^2$ is hydrogen, alkyl of 1 to 4 carbon atoms or phenyl;

$R^3$ is hydrogen or alkyl of 1 to 4 carbon atoms;

$R^4$ and $R^5$ are independently hydrogen, alkyl of 1 to 4 carbon atoms, alkoxy of 1 to 4 carbon atoms, phenylmethoxy, alkanoyloxy of 2 to 4 carbon atoms, hydroxy, halo, amino, mono- or dialkylamino in which each alkyl group has 1 to 4 carbon atoms, alkanamido of 2 to 6 carbon atoms or sulfonamido, or $R^4$ and $R^5$ together form methylenedioxy, ethylenedioxy, or propylenedioxy;

n is one of the integers 2, 3 or 4;

or a pharmaceutically acceptable salt thereof.

2. A compound of claim 1 in which $R^1$ is either hydrogen or taken with Z, $R^2$ is hydrogen and n is 2, or a pharmaceutically acceptable salt thereof.

3. A compound of claim 1 of the formula:

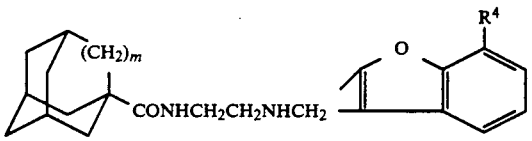

in which $R^4$ is —OH or —OCH_3; and m is 0 or 1;

or a pharmaceutically acceptable salt thereof.

4. The compound of claim 1 which is 3a,4,4a,6a,7,7a-hexahydro-2-[2-[[(7-methoxy-2-benzofuranyl)methyl]amino]ethyl]-4,7-etheno-1H-cyclobutisoindole-1,3(2H)-dione, or a pharmaceutically acceptable salt thereof.

5. The compound of claim 1 which is N-[2-[[(7methoxy-2-benzofuranyl)methyl]amino]ethyl]tricyclo[3.3.1.1^{3,7}]decane-1-carboxamide, or a pharmaceutically acceptable salt thereof.

6. The compound of claim 1 which is 8-[2-[[(7-methoxy-2-benzofuranyl)methyl]amino]ethyl]-8-azaspiro[4.5]decane-7,9-dione, or a pharmaceutically acceptable salt thereof.

7. The compound of claim 1 which is decahydro-3-[2-[[(7-methoxy-2-benzofuranyl)methyl]amino]ethyl]-1,5-methano-6,7,9-metheno-2H-pentaleno[1,2-d]azepine- 2,4(3H)-dione, or a pharmaceutically acceptable salt thereof.

8. The compound of claim 1 which is N-[2-[[(7-methoxy-2-benzofuranyl)methyl]amino]ethyl]-7,7-dimethyl-2-oxobicyclo[2.2.1]heptane-1-carboxamide, or a pharmaceutically acceptable salt thereof.

9. The compound of claim 1 which is N-[2-[[(7-methoxy-2-benzofuranyl)methyl]amino]ethyl]-4-fluorobenzamide, or a pharmaceutically acceptable salt thereof.

10. The compound of claim 1 which is N-[2-[[(7-methoxy-2-benzofuranyl)methyl]amino]ethyl]hexahydro-2,5-methanopentalene-3a(1H)-carboxamide, or a pharmaceutically acceptable salt thereof.

11. The compound of claim 1 which is N-[2-[[(7-methoxy-2-benzofuranyl)methyl]amino]ethyl]-1-methyl-1-cyclohexane carboxamide, or a pharmaceutically acceptable salt thereof.

12. The compound of claim 1 which is N-[2-[[(6,7-dimethoxy-2-benzofuranyl)methyl]amino]ethyl]tricyclo[3.3.1.1$^{3,7}$]decane-1-carboxamide, or a pharmaceutically acceptable salt thereof.

13. The compound of claim 1 which is N-[2-[[(7-methoxy-2-benzofuranyl)methyl]methylamino]ethyl]-tricyclo[3.3.1.1$^{3,7}$]decane-1-carboxamide, or a pharmaceutically acceptable salt thereof.

14. The compound of claim 1 which is N-[2-[[(7-methoxy-2-benzofuranyl)methyl]amino]ethyl]-2,2-dimethylpropanamide, or a pharmaceutically acceptable salt thereof.

15. The compound of claim 1 which is N-[2-[[(6-phenylmethoxy-2-benzofuranyl)methyl]amino]ethyl]-tricyclo[3.3.1.1$^{3,7}$decane-1-carboxamide, or a pharmaceutically acceptable salt thereof.

16. The compound of claim 1 which is N-[2-[[(7-fluoro-2-benzofuranyl)methyl]amino]ethyl]tricyclo[3.3.1.1$^{3,7}$]decane-1-carboxamide, or a pharmaceutically acceptable salt thereof.

17. The compound of claim 1 which is N-[2-[[(5-phenylmethoxy-2-benzofuranyl)methyl]amino]ethyl]-tricyclo[3.3.1.1$^{3,7}$]decane-1-carboxamide, or a pharmaceutically acceptable salt thereof.

18. The compound of claim 1 which is N-[2-[[(5-hydroxy-2-benzofuranyl)methyl]amino]ethyl]tricyclo[3.3.1.1$^{3,7}$]decane-1-carboxamide, or a pharmaceutically acceptable salt thereof.

19. The compound of claim 1 which is N-[2-[[(7-chloro-2-benzofuranyl)methyl]amino]ethyl]tricyclo[3.3.1.1$^{3,7}$]decane-1-carboxamide, or a pharmaceutically acceptable salt thereof.

20. The compound of claim 1 which is N-[2-[[(6-hydroxy-2-benzofuranyl)methyl]amino]ethyl]tricyclo[3.3.1.1$^{3,7}$]decane-1-carboxamide, or a pharmaceutically acceptable salt thereof.

21. A method for alleviating the symptoms of psychoses, depression or anxiety which comprises administering orally or parenterally, to a patient suffering from a CNS dysfunction treatable by an antipsychotic, antidepressant or anxiolytic agent an effective amount of a compound of the formula:

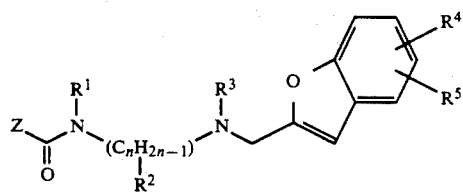

wherein
Z is phenyl or phenyl substituted with alkyl of 1 to 4 carbon atoms, alkoxy of 1 to 4 carbon atoms, hydroxy, halogen or methylenedioxy or Z is one of the structures

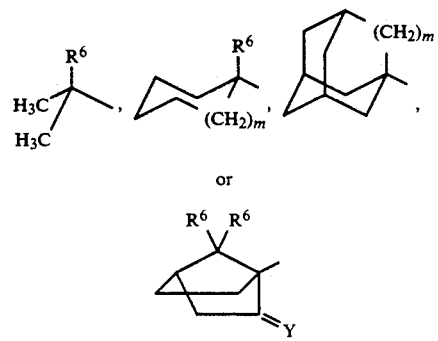

or in which
m is one of the integers 0, 1 or 2;
$R^6$ is hydrogen or alkyl of 1 to 4 carbon atoms;
Y is $H_2$ or O; or
Z, taken with $R^1$, forms one of the structures

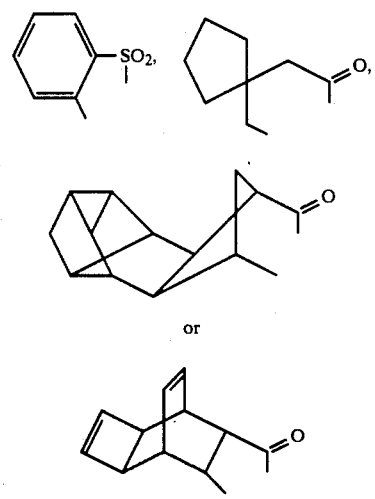

$R^1$ is hydrogen or alkyl of 1 to 4 carbon atoms;
$R^2$ is hydrogen, alkyl of 1 to 4 carbon atoms or phenyl;
$R^3$ is hydrogen or alkyl of 1 to 4 carbon atoms;
$R^4$ and $R^5$ are independently hydrogen, alkyl of 1 to 4 carbon atoms, alkoxy of 1 to 4 carbon atoms, phenylmethoxy, alkanoyloxy of 2 to 4 carbon atoms, hydroxy, halo, amino, mono- or dialkylamino in which each alkyl group has 1 to 4 carbon atoms, alkanamido of 2 to 6 carbon atoms or sulfonamido, or $R^4$ and $R^5$ together form methylenedioxy, ethylenedioxy, or propylenedioxy;
n is one of the integers 2, 3 or 4;
or a pharmaceutically acceptable salt thereof.

* * * * *